United States Patent [19]

Carson et al.

[11] Patent Number: 4,810,503

[45] Date of Patent: Mar. 7, 1989

[54] POLYMERS WHICH FORM GELS AT LOW CONCENTRATIONS IN WATER

[75] Inventors: James E. Carson, Lincoln Park; James P. Owens, Wyandotte, both of Mich.

[73] Assignee: BASF Corporation, Parsippany, N.J.

[21] Appl. No.: 33,334

[22] Filed: Mar. 31, 1987

[51] Int. Cl.$^4$ ................................................ A61K 7/00
[52] U.S. Cl. ...................................... 424/76.3; 424/78; 424/DIG. 8; 514/714; 514/715; 514/725; 514/772; 252/315.01; 252/315.1; 252/DIG. 1; 252/DIG. 5; 568/606; 568/579
[58] Field of Search ......................... 424/76.3, 78, D8; 514/714, 715, 725, 772; 252/D1, D5, 315.01, 315.1; 568/606, 579

[56] References Cited

U.S. PATENT DOCUMENTS

| | | |
|---|---|---|
| 3,954,882 | 5/1976 | Kalopissis et al. ............... 424/70 |
| 4,257,902 | 3/1981 | Singer ............................... 252/18 |
| 4,288,639 | 9/1981 | Camp ................................ 568/625 |
| 4,304,902 | 12/1981 | Landoll ............................. 528/419 |
| 4,312,775 | 1/1982 | Panek et al. ..................... 252/316 |
| 4,411,819 | 10/1983 | Panek et al. ................... 252/315.1 |
| 4,481,125 | 11/1984 | Holgado .......................... 252/75 |
| 4,521,326 | 6/1985 | Seibert et al. .............. 252/174.21 |
| 4,533,545 | 8/1985 | Sebag ............................... 424/70 |

Primary Examiner—John Kight
Assistant Examiner—S. A. Acquah
Attorney, Agent, or Firm—John C. Demeter; Bernhard R. Swick

[57] ABSTRACT

This invention relates to an aqueous gel comprising a specified capped polyether polymer and a surfactant. Preferred capped polyether polymers can be obtained by modifying a conventional polyether polyol with an alpha-olefin epoxide having an average of about 20 to 45 carbon atoms or mixtures thereof.

18 Claims, No Drawings

POLYMERS WHICH FORM GELS AT LOW CONCENTRATIONS IN WATER

BACKGROUND OF THE INVENTION

Clear aqueous gels are prepared from certain polyethers, surfactant and water. These gels are particularly useful in the formation of topically applied cosmetic and pharmaceutical compositions.

The prior art teaches that in order to form gels in formulations containing polyoxyethylene-polyoxypropylene block polymers, it is necessary to include a gelling agent. For example, U.S. Pat. No. 2,773,801 teaches the use of natural and synthetic gums and gum-like materials as gelling agents. British Pat. No. 786,346 teaches that it is necessary to treat a hydroxy polymer with a complex condensation product of one mole of a compound of the formula $Ti(OR)_4$, wherein R is an alkyl radical of 1 to 8 carbon atoms with $\frac{1}{2}$ to 4 moles of a saturated $C_2$–$C_6$, aliphatic hydroxy mono-, di-, or tri-carboxylic acid to obtain gellation. It has also been reported by W. Schonfeldt ("Surface Active Addition Products of Ethylene Oxide") that nonyl phenols with 40 or more moles of ethylene oxide added thereto do not form gels in an aqueous solution.

U.S. Pat. No. 3,639,574 relates to hydrogen peroxide gels prepared employing certain polyoxyethylene polyoxypropylene block copolymers as gelling agents. U.S. Pat. No. 3,740,421 relates to polyoxyethylene-polyoxypropylene aqueous gels. Polyoxyethylene-polyoxypropylene block copolymers form gels within certain specified ranges of compositions with water. U.S. Pat. No. 3,579,465 relates to polyoxyethylene-polyoxypropylene adducts of ethylene diamine which, within specified limits form aqueous gels.

The latter two patents required incorporation of the polyoxyethylene-polyoxypropylene compounds in amount of from about 20 to 90 weight percent in the gel composition.

U.S. Pat. No. 4,465,663 discloses the production of clear aqueous gels from polyoxybutylene-polyoxyethylene block copolymers employed in an amount of about 16 to 84 percent by weight. For economic reasons, it would be desirable to be able to produce gels from polyalkylene compounds with or without other surfactants wherein the amount of said compounds including any additional surfactants is much less than the minimum 16 percent of the above prior art patents, preferably below 5 percent.

Accordingly, it is a purpose of the instant invention to provide organic polymer gels particularly suitable for use in cosmetic and pharmaceutical formulations from polyoxyalkylene compounds and another surfactant.

SUMMARY OF THE INVENTION

This invention relates to an aqueous gel comprising water, a specified capped polyether polymer and a surfactant.

Preferred capped polyether polymers can be obtained by modifying a conventional polyether polyol with an alpha-olefin epoxide having an average of about 20 to 45 carbon atoms or mixtures thereof.

The conventional polyether polyols used to prepare these capped polyether polymers are well known in the art. Essentially they are prepared by reacting an initiator, having at least two active hydrogen atoms, with one or more epoxides having from 2 to 4 carbon atoms, in the presence of an oxyalkylation catalyst at increased temperatures and pressures according to technique well known in the art, such as those described in U.S. Pat. Nos. 4,411,819 and 4,288,639 which are hereby incorporated by reference into this specification. The particular conventional polyether polyol selected naturally will vary depending upon the use. It may be a homopolymer (preferably based upon ethylene oxide), a block copolymer (preferably with an ethylene oxide segment), or a heteric copolymer. These terms are familiar in the art and need no further explanation. The heteric copolymers are generally preferred because they are liquid at ambient temperatures.

DETAILED DESCRIPTION OF THE INVENTION

The capped polyether polymers employed in the gel compositions of this invention can be obtained by modifying conventional polyether pllyols, as intermediates with an alpha-olefin oxide having an average of about 20 to 45, preferably about 20 to 30 carbon atoms or mixtures thereof. The preferred capped polyether polymers have a molecular weight of about 10,000 to about 100,000 and preferably are one of the following:

(A) polyethers prepared by reacting ethylene oxide and at least one lower alkylene oxide having 3 to 4 carbon atoms with at least one active hydrogen containing compound having from 2 to 10 carbon atoms and from 2 to 6 active hydrogens to prepare a heteric or block copolymer intermediate and further reacting said copolymer intermediate with at least one alpha-olefin oxide having an average carbon chain length of about 20 to 45 preferably about 20 to 30 aliphatic carbon atoms and wherein said alpha-olefin oxide is present in the amount of about 0.3 to 10 percent by weight based upon the total weight of said polyether.

(B) polyethers prepared by reacting ethylene oxide with at least one active hydrogen compound having from 2 to 10 carbon atoms and from 2 to 6 active hydrogens to prepare a homopolymer intermediate and further reacting said homopolymer with at least one alpha-olefin oxide having an average carbon chain length of about 20 to 45 perferably about 20 to 30 aliphatic carbon atoms and wherein said alpha-olefin oxide is present in the amount of about 0.3 to 10 percent by weight based on the total weight of said polyether.

The preparation of polyethers is well known in the art. Generally, polyethers are prepared utilizing at least one lower alkylene oxide, an active hydrogen containing compound, and an acid or basic oxyalkylation catalyst at elevated temperatures in the range of about 50° C. to 150° C., preferably about 80° C. to 130° C., under an inert gas pressure, generally from about 20 to about 100 lbs. per square inch gauge.

Any suitable prior art alkaline oxyalkylation catalyst can be used in the practice of this invention. These include, for example, strong bases, such as sodium hydroxide, sodium methylate, potassium hydroxide, and the like; salts of strong bases with weak acids, such as sodium acetate, sodium glycolate, and the like and quaternary ammonium compounds, such as benzyl dimethyl cetyl ammonium compounds and the like. The concentration of these catalysts in the reaction mixture is not critical and may vary from about 0.1 percent to 5 percent by weight of the initiator compound.

An inert organic solvent may be utilized in the above-described procedures. The amount of solvent used is that which is sufficient to provide a suitable reaction medium and is generally on a molar basis, in excess of the total amount of the reactants. Examples of suitable solvents includes aliphatic hydrocarbons, such as hexane, heptane, isoheptane; aromatic hydrocarbons, such as benzene, toluene, xylene; chlorinated hydrocarbons, such as carbon tetrachloride, ethylene dichloride, propylene dichloride, and oxygenated hydrocarbons, such as diethyl ether, dimethyl ether, anisole, and the like.

In accordance with this invention, a conventional copolymer polyether polyol is prepared by preparing block or heteric intermediate polymers of ethylene oxide and at least one lower alkylene oxide having 3 to 4 carbon atoms as intermediates. These are then capped with the alpha-olefin epoxide to prepare the polymers of this invention. Ethylene oxide homopolymers capped with said alpha-olefin oxides are also useful as intermediates.

The heteric copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C. to 150° C., preferably from 80° C. to 130° C., under an inert gas pressure preferably from about 30 psig to 90 psig.

A block copolymer intermediate is prepared by reacting either the ethylene oxide or said alkylene oxide having 3 to 4 carbon atoms with said active hydrogen-containing compound followed by reaction with the other alkylene oxide.

The ethylene oxide and the alkylene oxides having from 3 to 4 carbon atoms are used is said intrmediates in amounts so that the resulting polyether product will contain at least 10 percent by weight, preferably about 70 percent to about 90 percent by weight, ethylene oxide residue. The ethylene oxide homopolymer intermediate is prepared by reacting ethylene oxide with said active hydrogen-containing compound. The reaction conditions for preparing the block copolymer and ethylene oxide homopolymer intermediates are similar to those for the heteric copolymer intermediate. The temperature and pressure are maintained in the above ranges for a period of about one hour to ten hours, preferably one to three hours.

If desired, a catalyst may be added to the reaction mixture prior to the ethylene oxide addition. Alkaline catalysts such as potassium hydroxide or acid catalysts such as boron trifluoride are useful, as is well established in the art.

As is well known in the art, polyethers are prepared utilizing an initiator compound which contains a reactive (or active) hydrogen atom. The term "reactive" or "active" "hydrogen atom" is well known and clearly understood by those skilled in the art. However, to remove any possible ambiguity in this regard, the term "reactive or active hydrogen atom," as used herein and in the appended claims, includes any hydrogen atom fulfilling the following two conditions:
1. It is sufficiently labile to open the epoxide ring of propylene oxide, and
2. It reacts with methyl magnesium iodide to liberate methane in the classical Zerewitinoff reaction (see Niederle and Niederle, Micromethods of Quantitative Organic Analysis, p. 263, John Wiley and Sons, New York City, 1946).

The active hydrogen atoms which will fulfill the above two conditions are normally activated by being a member of a functional group containing an oxygen atom, e.g., a hydroxyl group, a phenol group, a carboxylic acid group, etc. Alternatively, certain hydrogen atoms may be activated by proximity to carbonyl groups such as those found in cyanoacetic esters, acetoacetic esters, malonic esters, as is well known in the art. Generally, polyhydric alcohol initiators selected from the alkane polyols, alkene polyols, alkyne polyols, aromatic polyols, and oxyalkylene polyols are useful initiators. specific examples of base compounds which may be used in preparing the polyoxyalkylene polymers of the invention include ethylene glycol, 1,3-butylene glycol, oxalic acid, mono-, di-, and triethanolamine, butylamine, aniline, etc.

Of the alkane polyols such as ethylene glycol, propylene glycol, 1,4-butanediol, 1,2-butanediol, trimethylol propane, glycerol, 2,3,5,6-hexane tetrol, sorbitol, pentaerythritol, glucose, sucrose, and the like, polyhydric alcohols having about 2 to 10 carbon atoms and from about 2 to about 6 hydroxy groups are preferred initiators. Alkene polyols having about 2 to 10 carbons and from about 2 to 6 hydroxyl groups are also useful. The oxyalkylene polyols, such as diethylene glycol, triethylene glycol, tetraethylene glycol, dipropylene glycol, tripropylene glycol, and the like are also useful.

The alpha-olefin oxides which are utilized to modify the conventional polyether intermediate of the prior art are those oxides and the commercially available mixtures thereof generally containing an average of about 20 to 45, preferably about 20 to 30, carbon atoms. The amount of alpha-olefin required to obtain the more efficient capped polyethers of the invention is generally about 0.3 to 10 percent, preferably about 4 to 8 percent, of the total weight of the polyethers of the invention.

Since the preparation of heteric and block copolymers of alkylene oxides and ethylene oxide homopolymers are well known in the art, further description of the preparation of said polymers is unnecessary. Further details of the preparation of heteric copolymers of lower alkylene oxide can be obtained in U.S. Pat. No. 3,829,506, incorporated herein by reference. Further information on the preparation of block copolymers of lower alkylene oxides can be obtained in U.S. Pat. Nos. 3,535,307; 2,675,619; 2,677,700; 3,036,118 and 2,979,578 incorporated herein by reference.

The surfactants useful in the instant invention may be ionic or non-ionic and many surfactants and types of surfactants may be employed. While all sufactants may not be effective in the composition of the instant invention, the fact that many are effective makes it a simple matter for one skilled in the art to select such surfactant with a minimum of trial and error.

Among the preferred surfactants for the gel composition of the instant invention are those having the formula $$C_nH_{2n+1}O(CH_2CH_2O)_mH$$

The values for n and m will vary depending on the capped polymer and amount thereof employed. Effective surfactants are those wherein n is about 8 to 20 preferably about 12 to 16 and m is about 5 to 20, preferably about 6 to 12.

The amounts of capped polyether polymer and surfactant may be as little as 1.0 percent by weight or less of each depending on the type and amount of the other component. There appears to be no maximum amount of either component than that dictated by economic considerations. However, a purpose of the invention is to make a gel with the smallest amount of gelling components possible for economic reasons. Accordingly, the total amount of capped olymer and surfactant would generally not exceed 10 percent by weight.

The aqueous gels of the invention may include additional components in effective amounts, for example, various drugs such as anti-psoriasis drugs, vitamins, and other drugs, any or all of which can be included in these formulations using the above-described gel matrix as a means of supplying the drug to various areas of the body where they are most effective. The aqueous gels of this invention may include a deodorant or anti-perspirant such as those based on oxyquinoline salts, zinc oxide, etc., an astringent such as aluminum chlorohydrate; and an antiseptic such as hexachlorodihydroxydiphenylmethane. Also the gels of this invention may contain hydrogen peroxide; materials for treating plantars warts, such as canthardain, ingredients for treating athlete's foot, such as undecylenic acid; and insecticides such as N,N-diethyltoluimide.

To those skilled in the cosmetic and pharmaceutical arts, it will become apparent that these gels may be used in shampoos, in lanolin and oxyethylated lanolin-rich skin creams, and with mineral oil for skin and hair products.

The following examples will further illustrate the various aspects of the invention. Where not otherwise specified throughout this specification and claims, temperatures are in degrees centigrade, and parts, percentages and proportions are by weight.

EXAMPLES 1-32

Thirty-two compositions were prepared by weighing the capped polymer and the surfactat into the same container. Where either or both components were solid at room temperature, each was heated to about 100° F. to allow enough fluidity to weigh out a small amount of material. In such case, the mixture was also mixed with gentle heating. The mixing was continued until the two components were well mixed. Room temperature water was then added with stirring to the mixture while gentle heating was maintained. The temperature was controlled such as to ensure that the solution temperature remained below the cloud point for the particular solution. The ultimate solution in water contained the percentages of the capped polymer and of the surfactant shown in the table below, the balance being water. The product or solution was observed to determine whether or not gelling occurred, results of which are shown in Table I below.

TABLE I

| Example # | Capped Polymer | | Surfactant | | Product Form |
|---|---|---|---|---|---|
| | No. | % | No. | % | |
| 1 | 1 | 1.0 | 1 | 1.0 | Signs of Gel |
| 2 | 1 | 1.0 | 1 | 2.0 | In 1% mineral oil- Thin liquid |
| 3 | 1 | 2.0 | 1 | 0.75 | No gel |
| 4 | 1 | 2.0 | 1 | 1.0 | Gel |
| 5 | 1 | 2.0 | 1 | 2.0 | Gel |
| 6 | 1 | 2.0 | 1 | 3.0 | In water/2-propanol Very thin |
| 7 | 1 | 2.0 | 1 | 4.0 | Ringing Gel |
| 8 | 1 | 3.0 | 1 | 1.0 | Gel |
| 9 | 1 | 4.0 | 1 | 5.0 | Ringing Gel |
| 10 | 1 | 4.0 | 1 | 10.0 | Ringing Gel |
| 11 | 1 | 4.0 | 1 | 20.0 | Ringing Gel |
| 12 | 2 | 2.0 | 1. | 4.0 | Ringing Gel |
| 13 | 2 | 3.0 | 1 | 4.0 | Ringing Gel |
| 14 | 2 | 4.0 | 1 | 4.0 | Ringing Gel |
| 15 | 2 | 5.0 | 1 | 4.0 | Ringing Gel |
| 16 | 3 | 6.0 | — | 0.0 | Opaque Liquid |
| 17 | 3 | 4.0 | 1 | 4.0 | Viscous Liquid |
| 18 | 4 | 4.0 | 1 | 4.0 | Liquid |
| 19 | 4 | 5.0 | 1 | 2.0 | Viscous Liquid |
| 20 | 4 | 7.0 | 1 | 2.0 | Thick Liquid |
| 21 | 1 | 2.0 | 2 | 2.0 | Viscous Liquid |
| 22 | 1 | 2.0 | 3 | 4.0 | Gel |
| 23 | 1 | 2.0 | 4 | 4.0 | Thin Liquid |
| 24 | 2 | 4.0 | 4 | 4.0 | Liquid |
| 25 | 1 | 2.0 | 5 | 4.0 | Fluid |
| 26 | 1 | 2.0 | 6 | 4.0 | Fluid |
| 27 | 1 | 2.0 | 5/6 | 4.0 | Fluid |
| 87 | 1 | 1.0 | 7 | 1.0 | Thin Liquid |
| 98 | 1 | 2.0 | 7 | 2.0 | Gel |
| 30 | 1 | 4.0 | 7 | 2.0 | Gel |
| 31 | 1 | 4.0 | 8 | 4.0 | Thin Liquid |
| 32 | 1 | 2.0 | 9 | 2.0 | Thin Liquid |

The capped polymers of Table I above were prepared as follows:

CAPPED POLYMER #1

A conventional polyether derived from ethylene oxide and 1,2-propylene oxide in the weight ratio of 75 percent ethylene oxide and 25 percent 1,2-propylene oxide was prepared by reaction with trimethylol propane in two stages in a five-gallon, stainless steel autoclave. A polymer was first prepared by reacting a mixture of trimethylol propane, potassium hydroxide, 1,2-propylene oxide, and ethylene oxide for a period of 18 hours at 120° C. The reaction mixture was then cooled and the viscous liquid product removed from the reactor. The intermediate product had a molecular weight of about 2700.

In the second stage of reaction, 1720 g of this 2700 molecular weight intermediate product was charged to the five-gallon, stainless steel autoclave. This material was reacted with 11,608 g of an 85/15 mixture of ethylene oxide and 1,2-propylene oxide under a nitrogen atmosphere at 120° C. for 22 hours. The resulting product has a molecular weight of about 17,000. The reaction mixture was stripped under vacuum and heated to 130° C. 1050 grams of a mixture of alpha-olefin epoxides having an aliphatic chain length of 24 to 28 aliphatic carbon atoms was then added. The stirring and heating was continued for another 12 hours before the reaction mixture was cooled and the product transferred to a container for use in the gel compositions of the above table.

CAPPED POLYMER #2

The procedure and proportions for capped polymer #1 were followed except that 875 grams of a mixture of alpha-olefin oxides having a chain length of 20 to 24 aliphatic carbon atoms was utilized.

CAPPED POLYMER #3

The procedure and proportions for capped polymer #1 was followed utilizing the same proportions thereof with the exception that 710 grams of an alpha-olefin oxide having a chain length of 18 carbons was used to prepare the polymer.

CAPPED POLYMER #4

The procedure and proportions for capped polymer #1 were used except that 625 grams of alpha-olefin oxide having an aliphatic carbon chain length of 15 to 18 carbons was used.

The surfactants of Table I above were as follows:
Surfactants 1–6 have the following general formula $$C_nH_{2n+1}O(C_2H_4O)_mH$$

wherein for
surfactant #1—n is 14 and m is 8,
surfactant #2—n is 8, and m is 8,
surfactant #3—is a mixture wherein n ranges from 12 to 15 and m has an average of 8.3,
surfactant #4—n is 10 and m is 7,
surfactant #5—n is 9–11, and m is 6, (Neodol 91-6)
surfactant #6—n is 9–11, and m is 8, (Neodol 91-8)
The surfactant designated 5/6 is a 50/50 mixture of surfactant #5 with surfactant #6.

In the above surfactants, #1 and #2, $C_n$ is a linear carbon chain of n atoms while surfactants #4 thru #6 are made from a $C_n$ alcohol which is approximately 80 percent normal alcohol and 20 percent alpha-methyl alcohol in the case of surfactant #4 and 85 to 90 percent and 10 to 15 percent alpha-methyl alcohol for surfactants #5 and #6, respectively. In surfactant #3 $C_n$ is primarily linear but does contain a small percentage of an alpha-methyl component in the parent alcohol.

Surfactant #7 is sodium laureth-3 sulphate sold under the name STANDAPOL ES-3.
Surfactant #8 is a mixture of sodium lauryl sulphates sold by Henkel Incorporated under the name STANDAPOL WAQ-LC.
Surfactant #9 is dodecyl benzene sulphate.

EXAMPLES 33–40

Eight compositions were prepared in accordance with Examples 1–32 herein. The product or solution was observed to determine whether or not gelling occurred, results of which are shown in Table II below.

TABLE II

| Example # | Capped Polymer No. | % | Surfactant No. | % | Product Form |
|---|---|---|---|---|---|
| 33 | 1 | 2.0 | 1 | 4.0 | Ringing Gel |
| 34 | 2 | 2.0 | 1 | 4.0 | Ringing Gel |
| 35 | 3 | 2.0 | 1 | 4.0 | Viscous Liquid |
| 36 | 5 | 2.0 | 1 | 4.0 | Liquid |
| 37 | 1 | 2.0 | 2 | 2.0 | Viscous Liquid |
| 38 | 2 | 2.0 | 2 | 2.0 | Viscous Liquid |
| 39 | 3 | 2.0 | 2 | 2.0 | Viscous Liquid |
| 40 | 5 | 2.0 | 2 | 2.0 | Liquid |

By comparing Examples 33 and 34 with 35 and 36, it can be seen that where the polymer cap has an aliphatic chain length of 18 or fewer carbons, (Examples 35 and 36), no gel was formed but with those having a cap with an aliphatic chain length of 20 or more carbons, (Examples 33 and 34), ringing gels were formed. Examples 37 and 38 show that even with polymers having the cap of aliphatic chain length of 20 or greater, a gel is not formed with surfactant #2, which has a carbon atom chain of 8 carbons, in amount of 2 weight percent.

In Table II, capped polymers 1–3 are the same as described in connection with Examples 1–32. Capped polymer #5 was prepared by using the procedure and proportions for capped polymer #1, except that 640 grams of a mixture of alpha-olefin oxides having a chain length of 16 carbon atoms was utilized.

EXAMPLES 41–48

Eight more compositions were prepared by the method described in connection with Examples 1–32. The product or solution was observed to determine whether or not gelling occurred, results of which are shown in Table III below.

TABLE III

| Example # | Capped Polymer No. | % | Surfactant No. | % | Product Form |
|---|---|---|---|---|---|
| 41 | 1 | 2.0 | 10 | 2.0 | Soft Gel |
| 42 | 1 | 2.0 | 1 | 2.0 | Gel |
| 43 | 1 | 2.0 | 11 | 2.0 | Ringing Gel |
| 44 | 1 | 2.0 | 2 | 2.0 | Viscous Liquid |
| 45 | 2 | 4.0 | 10 | 2.0 | Gel |
| 46 | 2 | 4.0 | 1 | 2.0 | Ringing Gel |
| 47 | 2 | 4.0 | 11 | 2.0 | Viscous Liquid |
| 48 | 2 | 4.0 | 2 | 2.0 | Liquid |

In the above examples, particularly Examples 41, 43, 45, and 47, surfactants #10 and #11 have the same general formula as surfactants 1–6 set forth above in connection with Examples 1–32 but for surfactant 10 n is 16 and m is 8 and in surfactant 11, n is 12 and m is 8.

The data in Table III show that for the class of nonionic surfactants having the generalized formula set forth above for surfactants 1–6, the size of the hydrophobic alkyl chain affects the gellation behavior of the capped polymer surfactant system. With both capped polymers the strength of the gel appears to go through a maximum for the $C_{14}$-$C_{12}$ alkylethoxylates.

EXAMPLES 49–55

Seven compositions were prepared from 2 percent by weight capped polymer #1 with surfactant 1 in the percentages by weight shown in Table IV below. The product or solution was observed to determine whether or not gelling occurred, the results of which are shown in Table IV below.

TABLE IV

| Example # | Surfactant % | Product Form |
|---|---|---|
| 49 | 0.75 | Liquid |
| 50 | 1.0 | Gel |
| 51 | 2.0 | Gel |
| 52 | 4.0 | Ringing Gel |
| 53 | 6.0 | Ringing Gel |
| 54 | 10.0 | Viscous Liquid |
| 55 | 15.0 | Liquid |

The above table shows the gel characteristics of surfactant 1 at various percentage levels when combined with 2 weight percent of capped polymer #1.

EXAMPLES 56–58

Three compositions were prepared from 4 weight percent of surfactant #1 with capped polymer #1 in the percentages, set forth in Table V below. The product or solution was observed to determine whether or not gelling occurred, results of which are shown in Table V below.

TABLE V

| Example # | Capped Polymer % | Product Form |
|---|---|---|
| 56 | 2 | Ringing Gel |
| 57 | 4 | Ringing Gel |

TABLE V-continued

| Example # | Capped Polymer % | Product Form |
|---|---|---|
| 58 | 8 | Friable Gel |

There is no apparent upper limit to how much capped polymer #1 can be used and still provide gellation. The terminology "friable gel" refers to the nature of the product being very crumbly or brittle to the touch. Different properties of the gels can be tailored to different application requirements.

EXAMPLES 59-64

Six compositions were prepared as described in Examples 1-32 from capped polymer #1 in the amounts shown in Table VI below and surfactant 12 and 13, the amounts and percent by weight set forth in Table VI below.

TABLE VI

| Example # | Capped Polymer % | Surfactant No. | % | Product Form |
|---|---|---|---|---|
| 59 | 2.0 | 12 | 2.0 | Gel |
| 60 | 1.0 | 12 | 2.0 | Liquid |
| 61 | 2.0 | 12 | 4.0 | Gel |
| 62 | 2.0 | 13 | 2.0 | Gel |
| 63 | 1.0 | 13 | 2.0 | Liquid |
| 64 | 2.0 | 13 | 4.0 | Viscous Liquid |

The surfactants of Table VI may be described as having the same general formula as surfactants 1-6, where for each n is 15 and wherein for surfactant 12, m is 12 and for surfactant 13, m is 9. Both surfactants include alphamethyl functions.

EXAMPLES 65-80

Sixteen compositions were prepared from capped polymers 1 and 2 in the amount of 2 percent by weight in each example. Four ionic surfactants were employed in Table VII below identified by the numerals 7, 8, 15, and 16, each in the amount of 0.75 weight percent and 1.5 weight percent as shown in Table VII below. The product or solution was observed in each example to determine whether or not gelling occurred, the results of which are shown in Table VII below.

TABLE VII

| Example # | Capped Polymer No. | Surfactant No. | % | Product Form |
|---|---|---|---|---|
| 65 | 2 | 8 | 0.75 | Viscous Liquid |
| 66 | 2 | 8 | 1.50 | Liquid |
| 67 | 2 | 15 | 0.75 | Phase Sep. |
| 68 | 2 | 15 | 1.50 | Soft Gel |
| 69 | 2 | 16 | 0.75 | Gel |
| 70 | 2 | 16 | 1.50 | Gel |
| 71 | 2 | 7 | 0.75 | Gel |
| 72 | 2 | 7 | 1.50 | Gel |
| 73 | 1 | 8 | 0.75 | Viscous Liquid |
| 74 | 1 | 8 | 1.50 | Liquid |
| 75 | 1 | 15 | 0.75 | Soft Gel |
| 76 | 1 | 15 | 1.50 | Phase Sep. |
| 77 | 1 | 16 | 0.75 | Gel |
| 78 | 1 | 16 | 1.50 | Soft Gel |
| 79 | 1 | 7 | 0.75 | Gel |
| 80 | 1 | 7 | 1.50 | Gel |

Surfactant 15 and 16 are similar to the surfactants 7 and 8 described above. They are one and two mole ethoxylates, respectively, of sodium lauryl sulfate and are sold under the names STANDAPOL ES-1 and ES-2.

EXAMPLES 81-88

Eight compositions were prepared in the manner described for Examples 1-32 using the capped polymers indicated in Table VIII below in the percentages indicated and sodium lauryl sulphate as the surfactant in the percentages indicated in Table VIII below. The product or solutions were observed to determine whether or not gelling occurred, results of which are shown in Table VIII below.

TABLE VIII

| Example # | Capped Polymer No. | % | Surfactant % | Product Form |
|---|---|---|---|---|
| 81 | 2 | 2.0 | 0.25 | Soft Gel |
| 82 | 2 | 2.0 | 0.50 | Soft Gel |
| 83 | 1 | 2.0 | 0.25 | Liquid |
| 84 | 1 | 2.0 | 0.50 | Soft Gel |
| 85 | 2 | 4.0 | 0.25 | Ringing Gel |
| 86 | 2 | 4.0 | 0.50 | Ringing Gel |
| 87 | 1 | 4.0 | 0.25 | Phase Sep (Soft Gel Phase) |
| 88 | 1 | 4.0 | 0.50 | Ringing Gel |

The results in Table VIII show that the nonethoxylated surfactant, sodium lauryl sulphate, does form gels with both capped polymer 1 and 2 at lower surfactant levels.

EXAMPLE 89

A capped polymer is prepared the same as capped polymer #1 with the exception that the intermediate polymer prior to capping is a block polymer prepared by reacting propylene oxide with the initiator followed by reaction of the ethylene oxide, the percentages of propylene oxide and ethylene oxide being the same as for capped polymer #1. This intermediate product is then reacted with a mixture of alpha-olefin epoxides having an aliphatic chain length of 24 to 28 carbon atoms as described for capped polymer #1. A gel is then made up by mixing two percent of the capped block copolymer with 4 percent of surfactant #1, balance water.

EXAMPLE 90

A capper polymer is prepared similar to capped polymer #1 with the exception that the polymer to be capped is an ethylene oxide homopolymer prepared by reacting ethylene glycol with ethylene oxide in amounts sufficient to achieve a molecular weight of 17,000. This homopolymer is then reacted with an alpha-olefin epoxide having a aliphatic chain length of 24 to 28 carbon atoms as described above in connection with capped polymer #1. A gel is made as described in connection with Examples 1-32 by preparing a three-component mixture of two percent of the capped ethylene oxide homopolymer, four percent of surfactant #1 balance water. A gel is achieved.

EXAMPLE 91

A hand lotion is prepared having the following composition:

| Ingredient | Weight % |
|---|---|
| Capped Polymer #1 | 0.75 |
| Surfactant #11 | 1.50 |
| Glycerol | 22.50 |
| Ethoxylan 1685 | 3.75 |
| Propylene Glycol | 1.50 |

| Ingredient | Weight % |
| --- | --- |
| Vitamin E Oil | 0.375 |
| Perfume FD & O 512701 | 5 drops |
| Water | Balance to 100% |

The above hand lotion composition behaved like a "tubable gel".

In the above composition Ethyoxylan 1685 is a product marketed by Emery Industries and may be described as a 75 mole ethoxylate of lanolin used in the cosmetic industry as an emollient.

Perfume FD&O 512701 may be described as a white floral bouquet with jasmine and gardenia aroma commonly used in shampoo formulations as a perfume replacement.

EXAMPLE 92

A hairstyling gel is prepared having the following composition.

| Ingredient | % WT |
| --- | --- |
| Capped Polymer #2 | 2.0 |
| Surfactant #1 | 2.0 |
| Ethoxylan 1685 | 1.0 |
| Luviskol ® K30 | 2.0 |
| Perfume FD & O #512895 | 5 drops |
| Water (Deionized) | 97.0 |

The above composition is prepared by weighing capped polymer #2 and surfactant #1 into a tared beaker with a stir bar. The beaker is gently warmed to melt the solids and the Ethoxylan 1685 than weighed into the beaker and the mixture warmed with stirring. A ten percent solution of Luviskol K30 film former is then prepared by slowly adding it to a weighed amount of warm water with vigorous stirring until the solution is homogeneous. When the first mixture is homogeneous and well melted, half of the required amount of warm water is added with continuous stirring. Then 10 percent aqueous solution of the Luviskol K30 film former is added and the heating terminated. The remaining warm water is then added and stirring continued until the gel cools to warm temperature.

In the above composition, Ethoxylan 1685 is as set forth in Example 91.

Luviskol K30 is a product marketed by BASF Corporation which may be described as a polyvinyl pyrrolidone specifically formulated for cosmetic applications which is used extensively in hair setting formulations.

Perfume FD&O #512895 may be described as a citral floral amber bouquest used in shampoo formulations.

The embodiments of the invention in which an exclusive property of privilege is claimed are defined as follows:

1. A polyether having a molecular weight of about 10,000 to about 100,000 which is selected from the group consisting of
   (A) polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to about 45 aliphatic carbon atoms and wherein said alpha-olefin oxide is present in the amount of about 0.3 to 10 percent by weight based upon the total weight of said polyether.
   (B) polyethers prepared by reacting ethylene oxide with at least one active hydrogen-containing compound having from 2 to 10 carbon atoms and from 2 to 6 active hydrogens to prepare a homopolymer intermediate and further reacting said homopolymer with at least one alpha-olefin oxide having an average carbon chain length of about 20 to 45 aliphatic carbon atoms and wherein said alpha-olefin oxide is present in the amount of about 0.3 to 10 percent by weight based on the total weight of said polyether.

2. The polyether of claim 1 wherein said intermediate is a heteric copolymer.

3. The polyether of claim 2 wherein said alpha-olefin oxide has an average carbon chain length of about 20 to 30 carbon atoms and is present in the amount of about 0.3 to 10 percent of the total weight of said polyether.

4. The polyether of claim 3 wherein the proportion of ethylene oxide residue to the residue of said lower alkylene oxide is from about 70 to about 90 percent by weight of ethylene oxide residue to about 30 to about 10 percent by weight of said lower alkylene oxide residue.

5. The polyether of claim 4 wherein said lower alkylene oxide is propylene oxide.

6. The polyether of claim 1 wherein said intermediate is a block copolymer.

7. The polyether of claim 6 wherein said alpha-olefin oxide has an average carbon chain length of about 20 to 30 carbon atoms and is present in the amount of about 0.3 to 10 percent of the total weight of said polyether.

8. The polyether of claim 7 wherein the proportion of ethylene oxide residue to the residue of said lower alkylene oxide is from about 70 to about 90 percent by weight of ethylene oxide residue to about 30 to about 10 percent by weight of said lower alkylene oxide residue.

9. The polyether of claim 8 wherein said lower alkylene oxide is propylene oxide.

10. The polyether of claim 1 wherein said polyether is polyether (B) of claim 1.

11. The polyether of claim 10 wherein said alpha-olefin oxide has an average carbon chain length of about 20 to 30 carbon atoms and is present in the amount of about 0.3 to 10 percent of the total weight of said polyether.

12. A gel composition comprising the polyether of claim 1, a surfactant and water.

13. The gel composition of claim 12 wherein the amount of water is at least about 10 percent by weight.

14. The gel composition of claim 13 wherein said surfactant has the formula $$C_nH_{2n+1}O(C_2H_4O)_mH$$

wherein n is about 8 to 20 and m is about 5 to 20.

15. The gel composition of claim 12 wherein said polyether is the polyether of claim 3.

16. The gel composition of claim 12 wherein the polyether is the polyether of claim 7.

17. The gel composition of claim 12 wherein the polyether is the polyether of claim 11.

18. The gel composition of claim 12 additionally including an effective amount of oxyethylated lanolin.

* * * * *